US009828576B2

(12) United States Patent
Viasnoff et al.

(10) Patent No.: US 9,828,576 B2
(45) Date of Patent: Nov. 28, 2017

(54) CELL CULTURE

(71) Applicants: National University of Singapore, Singapore (SG); Centre National de la Recherche Scientifique, Paris (FR)

(72) Inventors: Virgile Nicolas Robert Viasnoff, Paris (FR); Qiushi Li, Singapore (SG)

(73) Assignees: National University of Singapore, Singapore (SG); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/416,330

(22) PCT Filed: Jul. 29, 2013

(86) PCT No.: PCT/SG2013/000313
§ 371 (c)(1),
(2) Date: Jan. 22, 2015

(87) PCT Pub. No.: WO2014/021778
PCT Pub. Date: Feb. 6, 2014

(65) Prior Publication Data
US 2015/0203809 A1    Jul. 23, 2015

(30) Foreign Application Priority Data
Aug. 1, 2012 (GB) .................................. 1213654.5

(51) Int. Cl.
| | |
|---|---|
| *C12N 1/12* | (2006.01) |
| *G01N 33/50* | (2006.01) |
| *C12M 1/12* | (2006.01) |
| *C12M 1/18* | (2006.01) |
| *C12N 5/00* | (2006.01) |
| *C12M 1/32* | (2006.01) |
| *C12M 1/00* | (2006.01) |
| *B01L 3/00* | (2006.01) |

(52) U.S. Cl.
CPC .............. *C12M 25/04* (2013.01); *C12M 1/18* (2013.01); *C12M 23/12* (2013.01); *C12M 23/20* (2013.01); *C12M 25/02* (2013.01); *C12N 5/0062* (2013.01); *C12N 5/0068* (2013.01); *G01N 33/5014* (2013.01); *B01L 3/5085* (2013.01); *C12N 2529/10* (2013.01); *C12N 2533/30* (2013.01); *C12N 2533/52* (2013.01); *C12N 2533/90* (2013.01); *C12N 2537/10* (2013.01); *C12N 2539/00* (2013.01)

(58) Field of Classification Search
CPC .............................. C12M 1/18; C12N 2539/00

USPC ........................................................... 506/9
See application file for complete search history.

(56) References Cited

U.S. PATENT DOCUMENTS

| | | | |
|---|---|---|---|
| 5,776,748 A * | 7/1998 | Singhvi ................ | B01J 19/0046 435/174 |
| 6,120,875 A | 9/2000 | Haumont et al. | |
| 6,821,107 B1 | 11/2004 | Hara et al. | |
| 6,844,184 B2 | 1/2005 | Kim et al. | |
| 6,893,850 B2 | 5/2005 | Ostuni et al. | |
| 2005/0069572 A1 | 3/2005 | Williams et al. | |
| 2005/0182349 A1* | 8/2005 | Linde ...................... | A01N 1/02 604/4.01 |
| 2005/0196861 A1* | 9/2005 | Nakamori ........ | C07K 14/43586 435/404 |

FOREIGN PATENT DOCUMENTS

| | | |
|---|---|---|
| JP | 2003-527615 | 9/2003 |
| JP | 2005-027598 | 2/2005 |
| JP | 2006-512154 | 4/2006 |
| WO | WO 96/15223 A1 | 5/1996 |
| WO | WO 01/70389 A2 | 9/2001 |
| WO | WO 2004/060426 A1 | 7/2004 |
| WO | WO 2006/052551 A2 | 5/2006 |

OTHER PUBLICATIONS

Kirby et al. (Human Molecular Genetics, 2002, vol. 11, No. 17, pp. 2061-2075).*
Fernandes et al., "High-Throughput Cellular Microarray Platforms: Applications in Drug Discovery, Toxicology and Stem Cell Research," *Trends Biotechnol.* 27:342-349, 2009.
Great Britain Search Report dated Nov. 30, 2012 (dated Dec. 3, 2012) for Application No. GB1213654.5.
Morel et al., "Microfluidic Stickers for Cell- and Tissue-Based Assays in Microchannels," *Lab Chip* 7:1011-1013, 2009.
Richter et al., "Spatially Controlled Cell Adhesion on Three-Dimensional Substrates," *Biomed Microdevices* 12:787-795, 2010.
Palanker et al., "Migration of Retinal Cells through a Perforated Membrane: Implications for a High-Resolution Prosthesis," *Invest Ophthalmol. Vis. Sci* 45:3266-3270, 2004.
JP 2015-525405 Notification of Reason for Refusal dated Jun. 27, 2017 (with English Translation) (12 pages).

* cited by examiner

*Primary Examiner* — Karla Dines
(74) *Attorney, Agent, or Firm* — Klarquist Sparkman, LLP

(57) ABSTRACT

The disclosure relates to the fabrication of a three dimensional [3-D] cell culture membrane comprising one or more functionalized surfaces adapted to provide cell culture conditions suitable for the analysis of proliferation, differentiation or function of cells, typically eukaryotic or prokaryotic cells.

20 Claims, 12 Drawing Sheets

A

T: BSA/PEG
S: Fibronectin
B: Fibronectin

T: BSA/PEG
S: Fibronectin
B: BSA/PEG

T: BSA/PEG
S: BSA/PEG
B: Fibronectin

B 4x magnification 10x magnification $N_l$ = number of occupied microwells without any dead cells
$N_o$ = number of microwells occupied by cell
$N_t$ = number of total microwells $N_f$ = number of microwells with functional BC
$N_o$ = number of microwells occupied by cell
$N_t$ = number of total microwells

CELL CULTURE

CROSS REFERENCE TO RELATED APPLICATIONS

This is the U.S. National Stage of International Application No. PCT/SG2013/000313, filed Jul. 29, 2013, which was published in English under PCT Article 21(2), which in turn claims the benefit of Great Britain Application No. 1213654.5, filed Aug. 1, 2012.

The disclosure relates to the fabrication of a three dimensional [3-D] cell culture membrane comprising one or more functionalized surfaces adapted to provide cell culture conditions suitable for the analysis of proliferation, differentiation or function of cells, typically eukaryotic or prokaryotic cells. The cell culture membrane is adapted for installation and use in existing cell culture plastic-ware for the growth of cells and also high resolution microscopic techniques. The multi-cell array form of the cell culture membrane also provides an efficient and cost effective means to reproducibly provide cells in culture which can be used in drug screening methods.

BACKGROUND TO THE INVENTION

The culturing of eukaryotic cells, for example mammalian cells, has become a routine procedure and cell culture conditions which allow cells to proliferate, differentiate and function are well defined. Typically, cell culture of mammalian cells requires a sterile vessel, usually manufactured from plastics (typically polystyrene), defined growth medium and, in some examples, feeder cells and serum. The feeder cells function to provide signals which stimulate cell proliferation and/or maintain cells in an undifferentiated state and can influence cell function. The culturing of mammalian cells has many applications and there are numerous in vitro assays and models where cell culture is used for experimentation and research; for example the use of cells in tissue engineering; the use of mammalian expression systems for the production of recombinant protein and the use of mammalian cells in the initial screening of drugs.

Mammalian cells are used in initial drug screening to determine whether a lead therapeutic (e.g. a small molecule agonist or antagonist, a monoclonal antibody, peptide therapeutic, nucleic acid aptamer, small inhibitory RNA) has efficacy before animal trials are undertaken. There is a need to provide improved cell culture systems in which mammalian cells can be cultured to provide a population of cells that are as far as technically possible close to their natural state to enable the analysis of cell proliferation, differentiation and function in a reliable manner.

Cell culture systems are known in the art and have been available to the skilled person for many years. For example, WO2010/005995 discloses micro-patterned co-culture systems as infectious disease analysis platforms. WO2003/014334 discloses an in vitro cell culture method which provides a culture regimen that allows prostate epithelial cells to form 3D prostate-like-acini which closely resemble prostate acini found in vivo. Furthermore, cell culture substrates are described in WO00/34454 which comprises microcellular polymeric materials. These polymers form reticulate structures of pores that interconnect with one another to provide a substrate to which cells can attach and proliferate.

Cell culture typically involves the growth of cells in monolayer culture under sterile conditions in closed cell culture vessels. An approach is to use either 2D protein patterning or 3D micro-wells. 2D protein patterning has been successfully and extensively used to control cell behaviour. In addition micro-well fabrication using silicon etched Si wafers [1, 2], glass [3], polydimethylsiloxane [PDMS] [4], elastomeric stamps [5], hydrogels such as agarose or PEG [6, 7], collagen [8] or Parylen films [9] and fibers [10] have been used for culturing single cells or a limited number of cells in a confined environment. However, the technique usually amounts to using the microwells as miniaturized petri dishes without taking advantage of the confinement of the cells in the well and the possibility of creating 3D protein coated niches. This is mostly due to the fact that chemical coating cannot be different on the sides, top and bottom of the well and can thus only provide a single chemical cue to the cells with little observed advantages over 2D patterned surfaces, at least for single cell culture. In addition, single-cell micro-well technology is not so suitable for high resolution imaging since it suffers from the image distortion created by the index change between the cell and the material used in formation of the micro-wells (e.g. a silica polymer have a refractive index around 1.45) [11].

The present disclosure is illustrated, by example but not by limitation, using primary hepatocytes. Our 3D differential surface coating allows the culture of primary hepatocytes as cell doublets with controlled bile canaliculi [BC] morphology useful in the analysis of drug metabolism. Our technique allows the culture of functional primary hepatocytes at the doublet level for at least 96 hours. In addition our technique offers a versatile standalone membrane that can be included in any standard cell culture device. The cell culture system herein disclosed can be applied to mammalian cells to provide a means to produce cell cultures that mirror more closely in vivo conditions providing a more reliable cell culture system that has applications, for example in tissue engineering, recombinant protein production and drug screening.

STATEMENTS OF INVENTION

According to an aspect of the invention there is provided three dimensional cell culture substrate comprising: a perforated membrane comprising a cured polymer adapted for cell culture characterized in that said membrane has at least two modified cell culture surfaces wherein the first surface comprises at least one cell culture agent and the second surface comprises a second, different cell culture agent, wherein said membrane enhances the proliferation and/or differentiation or function of cells associated with said membrane.

In a preferred embodiment of the invention said membrane comprises a plurality of perforations wherein said perforations are at least 5 μm-1000 μm in diameter; preferably about 20 μm-300 μm μm in diameter.

The aspect ratio is commonly known as the proportional relationship between the height and the characteristic lateral dimension of the features. In the context of the present disclosure, in relation to perforation dimensions, the aspect ratio is typically not greater than 2.

In a preferred embodiment of the invention said perforations are 10-50 μm in height; preferably 40 μm in height.

In a preferred embodiment of the invention said curable polymer is UV curable. Preferably said curable polymer is an acrylate based polymer.

Acrylate based polymers are well known in the art and include, for example, poly(methyl methacrylate [PMMA] the Norland Adhesive series of optical adhesives [NOA series; see http://www.norlandprod.com). Further examples include curable polymers with the desired optical properties can be obtained from My Polymer, for example My 132, 133, 136, 145, 147 which vary in refractive index.

In a preferred embodiment of the invention said cell culture agent and/or said membrane is further modified by inclusion of a cross-linking agent that facilitates the cross-linking of the cell culture agent to said membrane to provide a modified cell culture surface.

The provision of a modified cell culture surface will facilitate the growth and differentiation of cells applied to the membrane. The cell culture agents according to the invention are typically proteins or glycoproteins. Proteins involved in maintaining the proliferation and/or differentiation of cells are well known. For example, typical protein factors include extracellular matrix proteins such as fibronectin, laminins, collagens, cadherins and fibroblast growth factors but also included in the scope of the invention are monokines and cytokines which are, depending on cell-type, required to maintain cell proliferation and/or differentiation. In addition carbohydrate agents such as lectins are well known to be involved in promoting cell differentiation and forming cell to cell contacts between similar and dissimilar cell types.

In a preferred embodiment of the invention said membrane has a refractive index of between about 1.30 to about 1.50; preferably about 1.33 to about 1.45.

In a preferred embodiment of the invention said cell substrate comprises a network of interconnected cell culture microwells.

In a further preferred embodiment of the invention said network comprises a plurality of elongate cell culture microwells adapted to provide at least said first and second modified cell culture surfaces.

Preferably, said elongate microwells are at least 300 µm in length.

Preferably, said elongate microwells are at least 30 µm wide.

According to a further aspect of the invention there is provided a process for the micro-fabrication of a cell culture membrane comprising at least one cell culture micro well wherein said micro well is adapted with at least two functionalized cell culture surface comprising the steps:
  i) contacting the surface of a support with a substrate adapted by the provision of one or more raised projections wherein one or more of said projections contact the surface of said support;
  ii) apply a cell culture compatible polymer solution to said substrate wherein said polymer is curable;
  iii) curing the applied polymer to form a cell culture membrane;
  iv) removing said membrane from said substrate and contacting a first membrane surface with one or more cell culture agent;
  v) re-orienting said membrane to expose a second membrane surface; and contacting said second membrane surface with a second, different, cell culture agent; and optionally
  vi) repeating iv) and/or v) to further functionalize said cell culture membrane.

The substrate according to the invention can be silicon based, for example polydimethylsiloxane [PDMS] or elastomeric stamps. It will be apparent that the process according to the invention creates a three dimensional cell culture membrane with a large surface area which can have up to three functionalized surfaces which surfaces can be modified by a plurality of cell culture agents to provide a superior cell culture membrane. The cell culture compatible polymer is typically a UV curable polymer although alternative curing is encompassed by the invention, [e.g. heat].

In a preferred method of the invention steps ii)-vi) are further modified by the inclusion of a chemical cross-linking agent which facilitates the cross-linking of said cell culture agent to said cell culture membrane.

Preferably said chemical cross-linking agent is a heterobifunctional cross-linking agent.

Examples of cross-linking agents are known in the art. For example, the inclusion of acrylate based cross-linking agents such as alpha-acryloyl-omega-carboxy succinimidyl ester poly(ethylene glycol) also known as acryl-peg-N hydroxysuccinimide.

In a preferred method of the invention said agent is an alpha-acryloyl-omega-carboxy succinimidyl ester poly(ethylene glycol) and is included in step ii) of the process according to the invention.

In a preferred method of the invention said cell culture agent is a protein

In an alternative preferred method of the invention said cell culture agent is a carbohydrate.

In a further alternative method of the invention said cell culture agent is a lipid based agent for example a glycolipid.

In an alternative preferred method of the invention said agent is a poly-amino acid coating.

Poly-amino acids have properties that mimic proteins and in particular proteins to which cells can attach and grow. Poly-amino acids can be homopolymers or heteropolymers.

Examples of poly amino acids useful in cell culture include poly-L-ornithine and poly-L-lysine. Proteinaceous coatings are well known in the art. For example see Culture of Animal Cells, Ian Freshney, Wiley-Liss 1994.

In a preferred method of the invention said agent[s] is an anti-fouling agent.

Anti-fouling agents are known in the art and prevent the accumulation of cell debris created during cell culture. Examples of anti-fouling agents are PEG methacrylate or pluronic Acid™.

According to a further aspect of the invention there is provided a cell culture membrane obtained or obtainable by the method according to the invention.

According to a further aspect of the invention there is provided a cell culture vessel comprising a cell culture membrane according to the invention.

According to a further aspect of the invention there is provided a cell culture vessel according to the invention comprising at least one cell type and cell culture medium.

In a preferred embodiment of the invention said cell culture substrate is suspended and supported in said cell culture medium.

In a further preferred embodiment of the invention said cell culture substrate comprises one or more cell culture surfaces wherein said cell culture surfaces do not contact a cell culture vessel surface.

"Cell culture vessel" is defined as any means suitable to contain the above described cell culture substrate. Typically, an example of such a vessel is a petri dish; cell culture bottle or flask or multiwell culture dishes or well insert. Multiwell culture dishes are multiwell microtitre plates with formats such as 6, 12, 48, 96 and 384 wells which are typically used for compatibility with automated loading and robotic handling systems. Typically, high throughput screens use homogeneous mixtures of agents with an indicator compound that is either converted or modified resulting in the production of a signal. The signal is measured by suitable means (for example detection of fluorescence emission, optical density, or radioactivity) followed by integration of the signals from each well containing the cells, substrate/agent and indicator compound.

In a preferred embodiment of the invention said cell is a eukaryotic cell, for example a mammalian cell.

In an alternative preferred embodiment of the invention said mammalian cell is a rodent cell, for example a rat, mouse or hamster cell.

In an alternative preferred embodiment of the invention said mammalian cell is a primate cell; preferably said primate cell is a human cell.

In a preferred embodiment of the invention said mammalian cell is selected from the group consisting of: an epidermal keratinocyte, a fibroblast (e.g. dermal, corneal, intestinal mucosa, oral mucosa, bladder, urethral, prostate, liver) an epithelial cell (e.g. corneal, dermal, corneal; intestinal mucosa, oral mucosa, bladder, urethral, prostate, liver), a neuronal glial cell or neural cell, a hepatocyte or hepatocyte stellate cell, a mesenchymal cell, a muscle cell (cardiomyocyte or myotube cell), a kidney cell, a blood cell (e.g. CD4+ lymphocyte, CD8+ lymphocyte) a pancreatic β cell; or an endothelial cell).

In a preferred embodiment of the invention said cell is a hepatocyte.

In a preferred embodiment of the invention said cell is a cancer cell derived from cancerous tissue.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In an alternative preferred embodiment of the invention said cell is a stem cell.

In a preferred embodiment of the invention said stem cell is selected from the group consisting of: haemopoietic stem cell; neural stem cell; bone stem cell; muscle stem cell; mesenchymal stem cell; epithelial stem cell (derived from organs such as the skin, gastrointestinal mucosa, kidney, bladder, mammary glands, uterus, prostate and endocrine glands such as the pituitary); endodermal stem cell (derived from organs such as the liver, pancreas, lung and blood vessels); embryonic stem cell; embryonic germ cell; embryonal carcinoma stem cell.

In a preferred embodiment of the invention said embryonic stem cell/embryonic germ cell is a pluripotent cell and not a totipotent cell.

In an alternative preferred embodiment of the invention said cell culture vessel includes a feeder cell; preferably fibroblast feeder cells.

In a preferred embodiment of the invention said cell is a prokaryotic cell, for example a bacterial cell.

In a further preferred embodiment of the invention said cell is genetically modified by transfection with an isolated nucleic acid or expression vector to recombinantly express a selected nucleic acid in said cell.

In a preferred embodiment of the invention said nucleic acid or expression vector is adapted to express a reporter polypeptide.

The analysis of promoter activity in a cell can be conveniently monitored by fusing a promoter to a nucleic acid that encodes a "reporter" protein or polypeptide. Examples are well known in the art and include enzymes such as β glucuronidase. Reporters that are proteinaceous fluorophores are also known in the art. Green fluorescent protein, GFP, is a spontaneously fluorescent protein isolated from coelenterates, such as the Pacific jellyfish, *Aequoria victoria*. Its role is to transduce, by energy transfer, the blue chemiluminescence of another protein, aequorin, into green fluorescent light. GFP can function as a protein tag, as it tolerates N- and C-terminal fusions to a broad variety of proteins many of which have been shown to retain native function. Most often it is used in the form of enhanced GFP in which codon usage is adapted to the human code. Other proteinaceous fluorophores include yellow, red and blue fluorescent proteins. These are commercially available from, for example Clontech. A yet further example is firefly luciferase.

According to an aspect of the invention there is provided a method for the culture of cells comprising the steps of:
  i) providing a cell culture vessel comprising:
    a) cells;
    b) a cell culture substrate according to the invention;
    c) cell culture medium sufficient to support the growth of said cells; and
  ii) providing cell culture conditions which promote the proliferation and/or differentiation and/or function of said cells.

In a preferred method of the invention said cells are eukaryotic cells; preferably mammalian cells.

In a preferred embodiment of the invention said mammalian cell is a rodent cell, for example a rat cell.

In an alternative preferred method of the invention said mammalian cells are human.

In a preferred method of the invention said cells are hepatocytes.

In a preferred method of the invention said cell culture substrate is suspended and supported in said cell culture medium.

In a further preferred method of the invention said cell culture substrate comprises one or more cell culture surfaces wherein said cell culture surfaces do not contact a cell culture vessel surface.

According to a further aspect of the invention there is provided a method to screen for an agent wherein said agent affects the proliferation, differentiation or function of a cell comprising the steps of:
  i) providing a cell culture comprising at least one cell and a cell culture substrate according to the invention;
  ii) adding at least one agent to be tested; and iii) monitoring the activity of the agent with respect to the proliferation, differentiation or function of said cells.

In a preferred method of the invention said cell is a hepatocyte.

In a preferred method of the invention said screening method includes the steps of: collating the activity data in (iii) above; converting the collated data into a data analysable form; and optionally providing an output for the analysed data.

A number of methods are known which image and extract information concerning the spatial and temporal changes occurring in cells expressing, for example fluorescent proteins and other markers of gene expression, (see Taylor et al Am. Scientist 80: 322-335, 1992), which is incorporated by reference. Moreover, U.S. Pat. No. 5,989,835 and U.S. Pat. No. 9,031,271, both of which are incorporated by reference, disclose optical systems for determining the distribution or activity of fluorescent reporter molecules in cells for screening large numbers of agents for biological activity. The systems disclosed in the above patents also describe a computerised method for processing, storing and displaying the data generated.

The screening of large numbers of agents requires preparing arrays of cells for the handling of cells and the administration of agents. Assay devices, for example, include standard multi-well microtitre plates with formats such as 6, 12, 48, 96 and 384 wells which are typically used for compatibility with automated loading and robotic handling systems. Typically, high throughput screens use homogeneous mixtures of agents with an indicator compound which is either converted or modified resulting in the production of a signal. The signal is measured by suitable means (for example detection of fluorescence emission, optical density, or radioactivity) followed by integration of the signals from each well containing the cells, agent and indicator compound.

The term "agent" includes any small molecule, antibody, polypeptide, peptide, aptamer, double stranded or small inhibitory RNA. These can be an agonist or an antagonist. Small molecule antagonists include chemotherapeutic agents useful in the treatment of diseases such as cancer.

According to a further aspect of the invention there is provided a method to test the liver toxicity of an agent comprising the steps of:
  i) providing a cell culture comprising at least one hepatocyte cell and a cell culture substrate according to the invention;
  ii) adding at least one agent to be tested; and
  iii) monitoring the activity of the agent with respect to the proliferation, differentiation or function of said hepatocyte cells as a measure of toxicity of the agent.

In a preferred method of the invention said agent is a chemotherapeutic agent.

In an alternative method of the invention said agent is a virus, for example a viral gene therapy vector.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1: Microwell fabrication and coating process (A) Schematic representation of the microwell fabrication process. A PDMS stencil is fabricated using classical soft lithography process (step 1) and placed on a flat substrate. The gaps are filled by capillarity (step 2) with a UV prepolymer mix (NOA 64). After UV curing, the stencil is removed and the NOA Membrane is incubated a solution of protein that will eventually coat the sides of the wells (step 3-4). The membrane is rinsed, dried and flipped onto a glass slide coated with the protein to be localized at the bottom of the wells (step 5-7). Pluronic acid was eventually used to passivate the top part of the wells (step 8-9). (B) Picture of microwell membrane in a 12 mm glass-bottom dish (scale bar=1 cm). (C) DIC image of hepatocytes in microwells (scale bar=100 µm). (D) Confocal images of the spatially structured coating of microwells. Pluronic acid (P, green, Alexa 488) and fibronectin (F, red, Alexa 561) were used. X/X indicates a side/bottom order of coating, where X is either F or P. (scale bar=5 µm)

FIG. 2: A: Confocal imaging of circular wells (30 µm in diameter, 40 µm in height) with various differential coatings. Green: BSA-GFP+PEG, Red: Fibronectin-Alexa 568. B: Bright field image of the seeding density at 4× and 10× magnification. Hepatocytes were seeded at 0.5 million/ml and gently stirred according to the described protocol;

FIG. 3: Cell survival assay. Fraction of microwells with all cells alive as a function of time. All conditions are represented with both polymers and three coating combination. In NOA wells the survival probability hardly depends on the coating combination and is clearly larger than for the MyPoly133;

FIG. 4: Effects of the differential coating on the hepatocytes doublet morphology and shapes. Fixed samples with actin in green (phalloidin-Alexa 488), nucleus blue (DAPI) and MrP2 in red (antibody-Alexa 568). A: Hepatocytes doublet adhering on sides and bottom present a bile canaliculi with branched morphology (possibly due to the internal tension generated by the actin stress fibers). If only the bottom cell can adhere to the substrate the bile canaliculi rounds. B: If the cells attach only to the side the bile canaliculi is formed mainly vertically as demonstrated from the z projection on the right panel. This orientation is very useful to study accumulation of proteins from the cytoplasm;

FIG. 5: 3D organization of cell-ECM adhesion influences the orientation of hepatocyte couplets and the BC morphology. 3D side views (right column, green, F-actin; blue, nucleus) and Z projection (middle column) of hepatocytes couplets culture for 2 days in the microwells with various coatings (left column) are demonstrated in (A-C). Couplets in F/F (A, n=39) and P/F (B, n=48) formed predominantly horizontal bile canaliculi. In F/P (C, n=44) the BC were mostly vertical. BC in F/F (A, XY) displayed in vivo-like tubular shape; in P/F (B, XY) they expanded into spherical shape. White dashed lines are virtual microwell boundaries for visual guidance. (scale bar=5 µm) (D) Quantitative analysis of BC orientation compared to microwell bottom. The parallel orientation corresponds to a null angle. (**, t-test, p<0.05);

FIG. 6: Perturbations of cell-ECM adhesion or actomyosin contractility drive BC into spherical shape in F/F microwell. Treatment of (A) soluble RGD (250 µM for overnight), (B) blebbistatin +/− (100 µM for 4 hours), or (C) Y27632 (10 µM for 4 hours) converted tubular BC into spherical ones (blue, nucleus; green, F-actin; scale bar=5 µm). (D) Classification of BC morphologies according to the dimensionless morphological index and vertical aspect ratio. BC in control F/F wells (yellow circles, n=35) clearly display a higher degree of folding r with flatter tubular shape (low i) as compared to cells treated with soluble RGD (blue triangles, n=39), blebbistatin (green diamonds, n=44) or Y27632 (purple triangles, n=42). Drug treatments led BC morphology in F/F microwells to be undistinguishable from that in P/F coating (red squares, n=37);

FIG. 7: Physical constraint combined with specific 3D ECM organization directs BC elongation via actomyosin contractility. Typical BC shapes stained with F-actin (i) and probability map of BC in microwells with different shapes (ii) on day 2. BC centers (black circles) and most distant apex of BC (white triangle) are overlaid. Circular F/F microwells (A, n=35) led to isotropically folded BC, whereas couplets cultured in F/F triangular microwells (B, n=29) formed BC with branches predominantly protruding towards the three vertices. BC elongated mainly along the long axis of F/P elongated microwells (C, n=46) containing ~6 hepatocytes. Note the relative absence of BC protrusions along the short axis. (scale bar=5 µm);

FIG. 8 Hepatic cord-like network of BC formed in intersecting elongated microwells with F/P coating. (A) Phase contrast image of hepatocytes inside intersecting elongated microwells (300 µm for each cross length) containing ~60 hepatocytes on day 2. (B) Fluorescent image of CLF at the same view of (A). (C) Immunostaining image of bile canaliculi network formed in intersecting elongated microwells. F-actin (Green) and nucleus (Red) were stained. Note the relative absence of transverse BC. (D) Surface rendering image of (C). F-actin (Green) and pan-Cadherin (Red) were presented. (E) Zooming-in on one branch of (D). (scale bar=30 µm);

MATERIALS AND METHODS

Micro Well Fabrication

Figure 1:
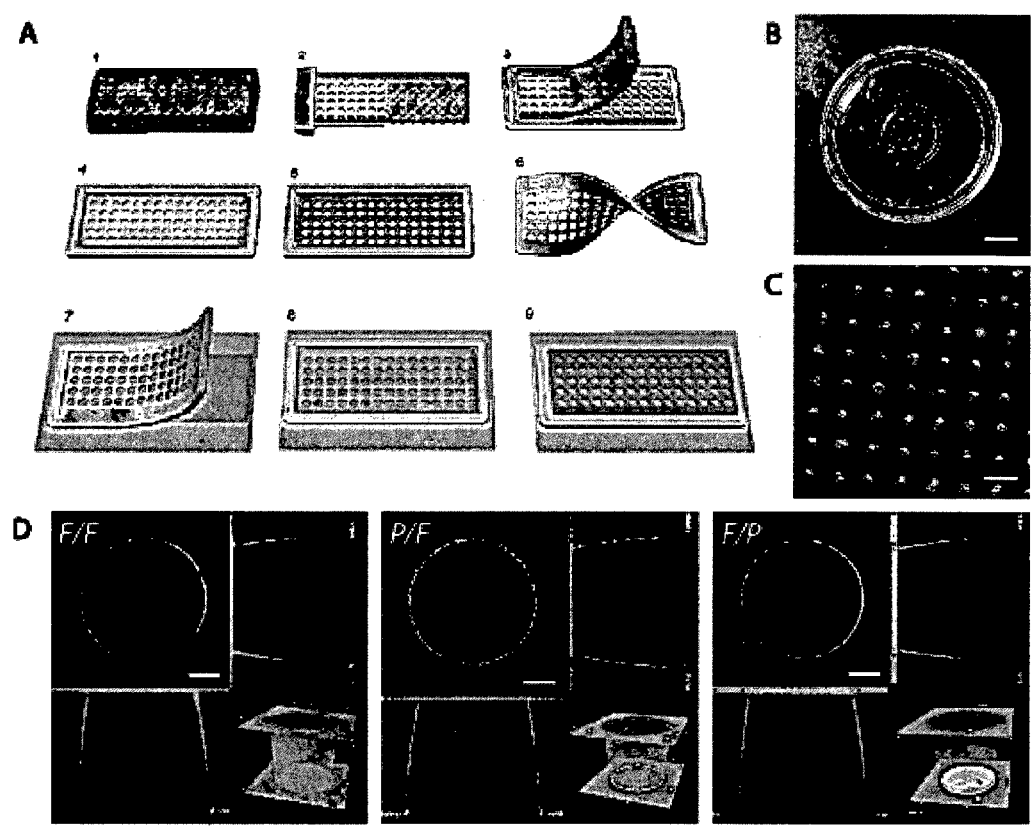

An elastomeric stamp (Poly dimethysiloxane PDMS) is fabricated using standard soft lithography methods onto a silicon wafer coated with SU8. The typical size of the stamp features are between 20 and 40 µm both in height and width.
1 Cut out a piece of PDMS with pillar feature. Do not leave any flat surface around pillar features to allow efficient capillary filling at the next steps.
2 Put the PDMS piece onto a petri dish with pillars against the surface of petri dish. Use a stick to pick polymers and drop a little on one side of PDMS. Polymers would flow in between pillars by capillary effect.
3. Start UV lamp and allow the lamp to warm up for 15 min. After the polymer filled the spaces between pillars, put more polymers around the PDMS stamp.
4. Shine UV light onto the PDMS and polymers for 20 s if NOA is used or 5 min if Mypoly133 is used. Peel off the PDMS piece from the cured polymer sheet with knife. Microwells are formed in the polymer membrane.
5 Add a drop of a solution A containing the agent you wish to coat the inside of the wells with onto the polymer sheet; typically fibronectin at 1 µg/ml or 0.2% pluronic Acid™. Collagen, cadherins and carbohydrates and poly functional PEG can also be used.
6. Vacuum for 10 minutes to degas air trapped in the micro-wells and allow solution A into them.
7. Incubate micro-well with solution A for 1 h at room temperature.
8. Incubate a suitable container [e.g. glass, silica, plastics] with a solution B containing the agent that will coat the bottom surface of the wells for 1 h at room temperature. Typically the same agents used for the sides can be used here. Additionally clean glass can be used if supported lipid bilayers are to be further formed at the bottom of the micro-wells.
9. Rinse the micro-well and glass bottom dish with water for 3 times.
10. Suck up water and air dry the micro-well and glass bottom dish.
11. Cut off edges of polymer sheet. Peel the sheet off from petri dish and reversely lay it in glass bottom dish, press the polymer sheet gently with a flat PDMS.
12. Passivate the top of polymer sheet with 0.2% pluronic Acid™ for 30 min. 1% PEG/Methacrylate can also be used at that stage. Followed by a 1 min exposure under UV to ensure covalent bonding to the unreacted acrylate groups at the polymer surface.
13. Rinse polymer sheet with water for 3 times.
14. Keep polymer sheet in water and vacuum it for 10 minutes.
15. Rinse polymer sheet with water for 3 times. UV treat polymer sheet for more than 15 min for sterilization.

Cell Seeding
1. Exchange PBS in uWell with cell culture medium. Incubate it in 37 degree Celsius.
2. Seed 0.5 million hepatocytes for each dish. Distribute hepatocytes evenly by shaking the dish back and forth. Put the dish gently into incubator.
3. After 15 minutes of incubation, shake the dish again and put the dish gently into incubator.
4. Repeat step 3 twice.
5. Wash the dish with PBS twice and add cell culture medium.

Cell Culture

Cells are cultured in 5% $CO_2$ and 37 degree Celsius. Cell culture medium is changed on daily basis. Here a specific medium, William's E medium is used for cell culture. 0.1% BSA, 2 mM L-Glutamine, 100 nM dexamethasone, 100 unit/ml penicillin, 0.1 mg/ml streptomycin, 0.05 µg/ul linoleic acid and 0.3 µg/ml insulin are supplemented into William's E medium.

Hepatocyte Isolation, Seeding and Culturing

Hepatocytes were isolated from male Wistar rats by a two-step in situ collagenase perfusion method, as described in [33]. Animals were handled according to the IACUC protocol approved by the IACUC committee of the National University of Singapore. With a yield of >108 cells/rat, viability of the hepatocytes was tested to be >90% by Trypan Blue exclusion assay.

Freshly isolated rat hepatocytes (0.5 million) were seeded onto microwells within 35 mm-glass bottom dish and cultured in 2 ml of William's E culture medium supplemented with 2 mM L-Glutamine, 1 mg/ml BSA, 0.3 µg/ml of insulin, 100 nM dexamethasone, 50 µg/ml linoleic acid, 100 units/ml penicillin, and 100 mg/ml streptomycin, all of which were purchased from Aldrich-Sigma in Singapore. Cells were incubated with 5% $CO_2$ at 37° C. and 95% humidity. After 1 h incubation, culture medium containing the unattached cells was removed. The microwells were rinsed with PBS and replenished with fresh culture medium. After 1 h, another 0.5 million hepatocytes were added and incubated for 1 h. The unattached cells were removed by PBS rinsing and culture medium was replenished again. Culture medium was changed on a daily basis.

Forming the Membrane and Index Matching

First we form membranes with through holes according to the protocol as described. The membrane is fabricated either in NOA 73, a low viscosity UV curable resin from Norland Adhesive or in MyPoly 133 DC another UV curable resist from My polymer with a refractive index matched with that of water. NOA 73 is used preferentially for long term culture since it does not release solvent in the culture medium in the long run. MYPoly 133 is used for short term culture and high resolution imaging. When index matching with the medium is expected to be very good, MYPOLy 133 can be mixed with Mypoly134 in adequate proportions to obtain an index of 1.338 matched with DMEM media. The proportions of both polymers are adjusted accordingly with the media index or the wave length used. An alternative approach is to make the membrane in MYpoly 134 and complement the culture medium with Sucrose or Sorbitol until index matching of 1.34 is achieved.

Viability Test and Bile Canaliculi Secretory Function Test

Hepatocyte viability was assessed daily with propidium iodide (Sigma, 81845 FLUKA), a dye that only stains the dead cells. 5 µM PI in culture medium was incubated with hepatocytes in microwells for 30 mins at 37° C. After rinsed with PBS, the stained cells were kept in culture medium and observed under wide-field EVOS microscope (Life Technology). Viability ratio was calculated as the number of microwells with dead cells over the number of all microwells.

Bile canaliculi [BC] secretion was assessed daily with CLF (BD, 451041), a dye that can only be secreted into functional bile canaliculi, where it becomes fluorescent. 5 µM CLF in culture medium was incubated with hepatocytes in microwells for 30 min in 37° C. After rinsing with PBS, the stained cells were kept in culture medium and observed under wide-field EVOS microscope. Functional bile canaliculi ratio was calculated as the number of microwells with functional bile canaliculi over the number of all microwells.

Immunostaining and Image Acquisition

For control, hepatocytes cultured for 48 hours in microwells were fixed in 4% para-formaldehyde (PFA) for 30 minutes. For ±Blebbistatin (Merck, 203390) or Y27632 (Sigma, Y0503) treatments, drugs were added 4 h before fixation, while soluble RGD (Sigma, G5646) was incubated with hepatocytes overnight. After fixation, the cells were rinsed by PBS and permeabilized for 30 min in TBST (0.2% Triton-X in TBS). The permeabilized cells were blocked with 1% BSA in TBST for 4 h and incubated overnight with pan-Cadherin antibody (sigma, C1821) and anti-ZO-1 antibody (life technology, 61-7300) at 4° C. as instructed in manuals. After rinsed with TBST, the cells were incubated in secondary antibodies (Life Technology, A10040 and A-31571) and phalloidin-alexa 488 (Life Technology, A12379) for 1 h in dark at room temperature. After rinsed with TBST again and incubated shortly with DAPI (Sigma, D9564), cells were mounted in mounting medium (DAKO, S3023). 3D stack of confocal microscopy images were acquired with 100×NA1.4 oil lens on a Nikon A1R Confocal Microscope.

Image Analysis

Figure 11:
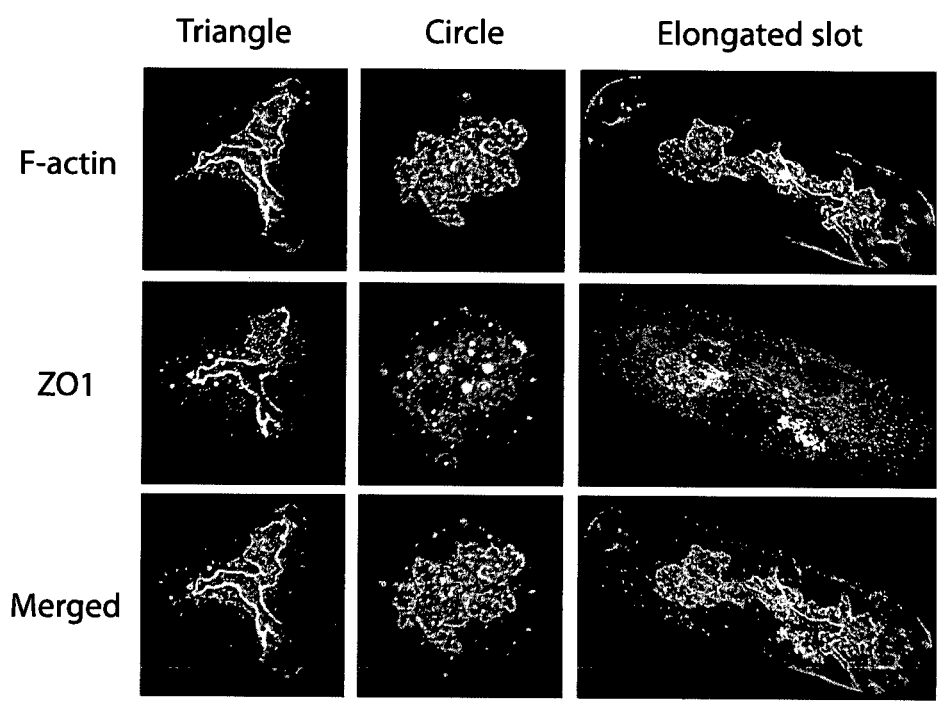
FIG. 11 illustrates the staining of F-actin and ZO-1 in the microwell device.

The selected slices of image stacks were reconstructed as maximum intensity projection or orthogonal section view. Manual segmentation was applied based on F-actin signal, because F-actin provides a better definition of BC boundaries, compared with ZO-1 (FIG. 11). Several features, such as parameter, thickness, horizontal spin size and area of bile canaliculi, were extracted subsequently.

For bile canaliculi morphology analysis in triangle and elongated microwells, bile canaliculi were extracted and converted into binary images. All of these binary bile canaliculi were aligned according to the microwell orientation and overlaid together in sum. Resultant image was color-coded based on the probability of bile canaliculi appearance. The warmer the color is, the more frequent the bile canaliculi appear at the specific location.

Statistical Analysis

Data from at least 3 independent experiments were analysed, and values were represented as mean±standard error of means. The number of samples in each group was presented individually in the graphs. The Student t-test was used to analyse the statistical significance of the data. Values with a p-value less than 0.05 were considered statistically significant.

Example 1

3D Micro-Patterning of ECM Protein on a Chip

To organize cell-ECM adhesion in 3D, we developed a new method to create microwells (FIG. 1) using standard soft lithography methods to fabricate a thin membrane (5-40 µm) with through holes [24]. A PDMS stamp was micro-moulded onto a textured wafer with microwells formed in SU8. The stamp was placed on a flat PDMS surface and the lumen was filled with NOA 64, a UV curable polymer. 30 s exposure (300 W Newport UV lamp operated at 20 mW/cm$^2$ at 400 nm) is enough to form a solid film that can subsequently be used as a sticker [28]. The stamp was subsequently peeled. We then achieved three different coating configurations: F/F, F/P, P/F labelled according to Side/Bottom order where F stands for fibronectin and P for pluronic acid. The differential coating was achieved as listed below (FIG. 1) using a 10 µg/ml fibronectin and 0.2% pluronic acid solutions.

i—Coating of the sides was achieved first. We incubated the membrane with the appropriate aqueous solution for 1 h. Degassing under vacuum was used to remove air bubbles trapped in the microwells. The membrane was subsequently rinsed and gently air-dried.

ii—Coating of the bottom was achieved by incubating an acid-washed coverslip with desired solution for 1 h. The microwell membrane was flipped over and laminated onto the dried coverslip.

iii—The top of the membrane was subsequently passivated for 1 h using pluronic acid. It ensures minimal adhesion of hepatocytes to the membrane top and maximal spontaneous localization of cells into the wells. The system was then sterilized under UV without appreciable loss of fibronectin (tested by spreading assay with MDCK cells, data not shown).

Figure 9:
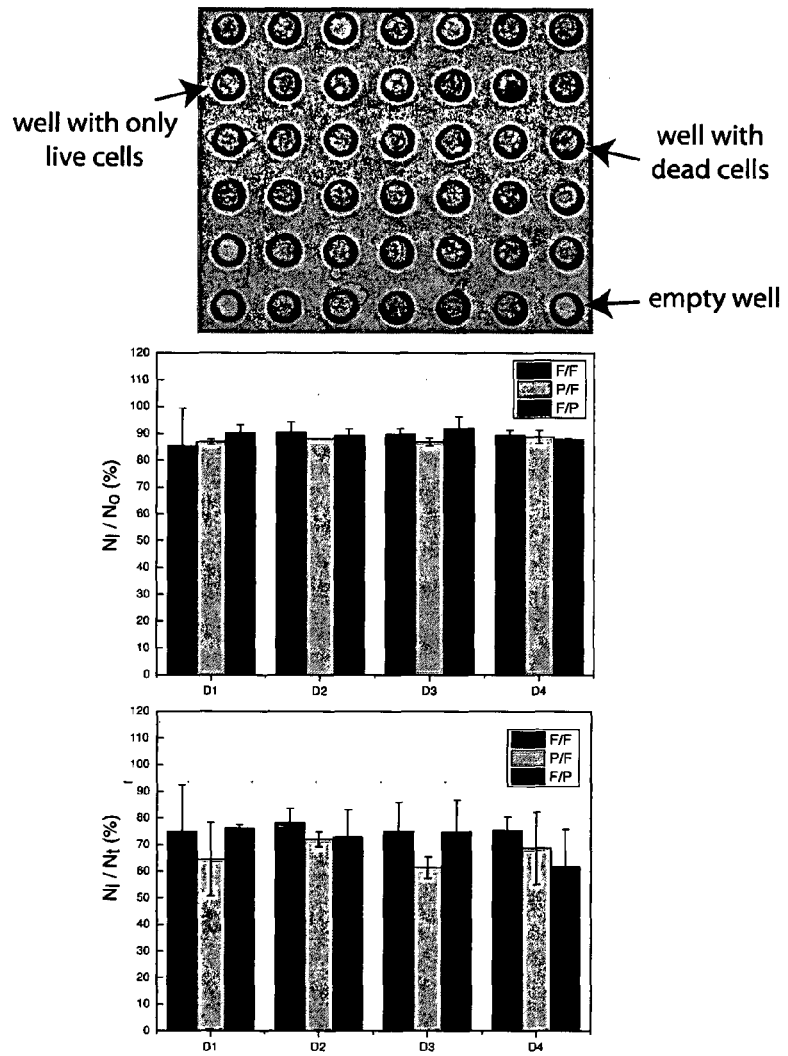
FIG. 9 illustrates the viability of hepatocytes in the microwell device.

Cell viability was assessed daily in each of the three coating configurations for 4 days using propidium iodide. The viability index was computed as the ratio of the number of microwells with no dead cells over the total number of microwells (FIG. 9). The survival rate was ~70% after 4 days independent of the coating configuration.

Figure 10:
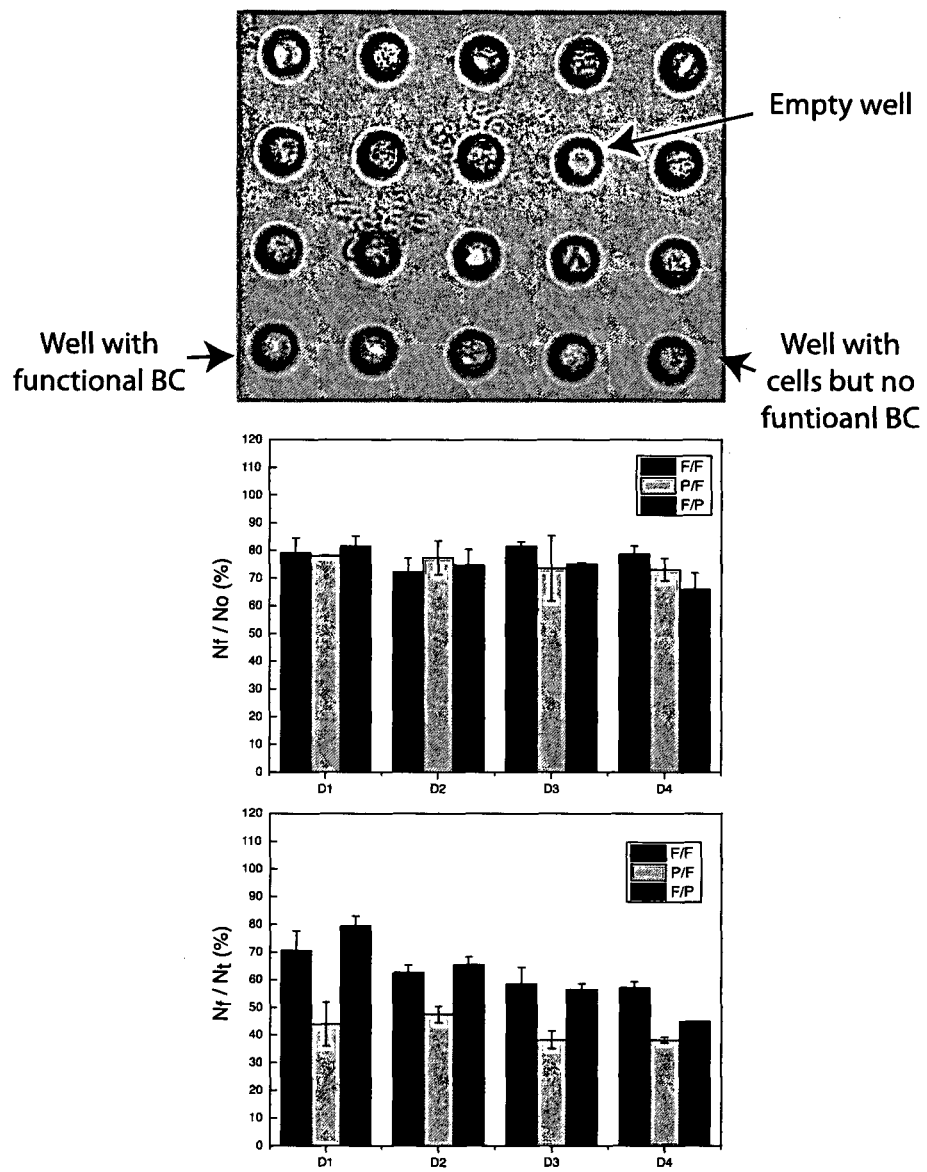
FIG. 10 illustrates the functionality of bile canaliculi in the microwell device.

We then tested the maintenance of functional BC over 4 days (FIG. 10). A functionality index was computed as the ratio of the numbers of microwells displaying functional BC stained by choly-lysyl-fluorescein (CLF) over the total number of microwells. Typically 50% to 70% of the total number of wells displayed a functional BC. After 3 days, cells gradually detached from the substrates for any coating configuration. It is most likely due to enzymatic degradation of fibronectin coated on microwells. However, 75% of remaining couplets was functional. We performed all experiments on day 2 when BC have reached their equilibrium shapes (no difference compared to day 4) and when hepatocyte attachment is still unperturbed.

Example 2

Figure 2:
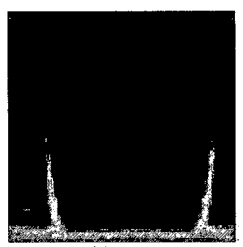
Figure 2:
Figure 2:
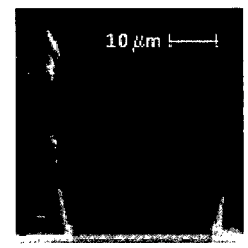
Figure 2:
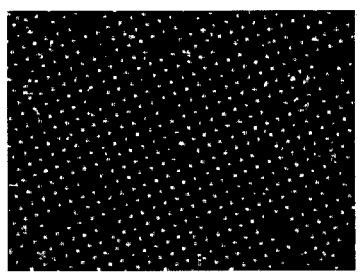
Figure 2:
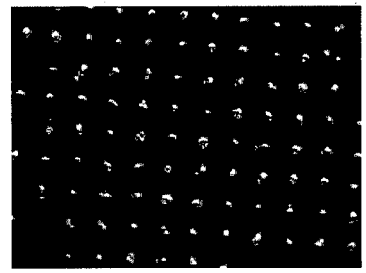
Figure 3:
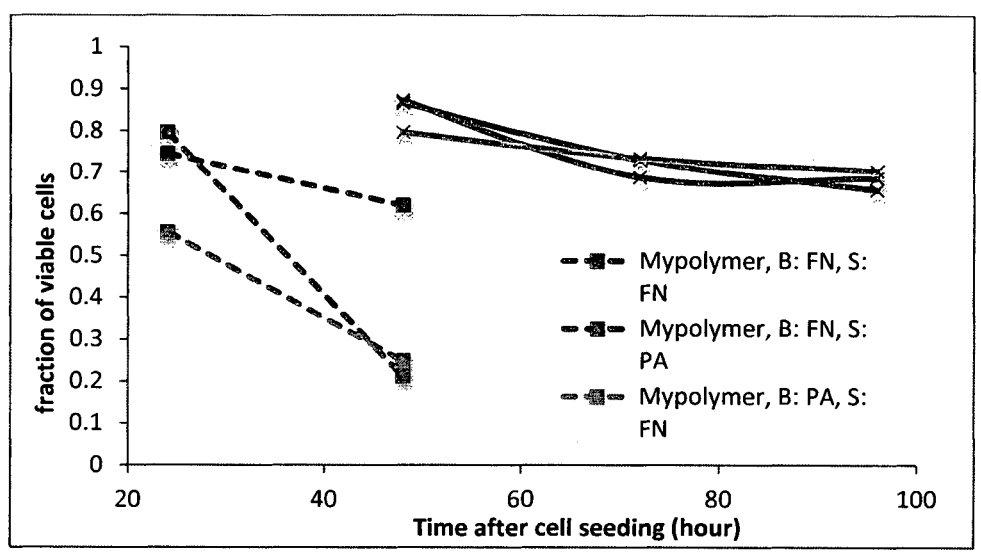

FIG. 2 illustrates the various combinations we used. Various other combinations where tested including BSA, cadherins and collagen. Though they are possible they are not used for hepatocyte cultures. The protein coating is mainly due to protein adsorption. Using a heterobifunctional PEG molecule Acrylate-PEG-NHS from NANOCS (nanocs.com), we are currently investigating the possibility to perform a direct chemical grafting. The acrylate moiety reacts with the polymer under UV curing and the NHS moiety is a standard functional group for protein functionalization.

Example 3

Primary hepatocytes freshly obtained from rat liver according to [22], are seeded at a density of 0.5 million/mL onto the Petri dish. Protecting the top of the membrane with an antifouling treatment is a key component to help cells fall in the wells. Failure in the antifouling treatment will result in cells attaching to the membrane top and not falling in the microwells. The seeding is followed by a gentle shaking procedure described in protocol to ensure the maximum well filling capability. Following this protocol 90% of the wells are filled with at least one cell and 70% are filled with at least two. Better optimization of the doublet rate is under current investigation.

The viability of the cells was tested daily since 24 h after cell seeding with propidium iodine solution (Sigma). In microwells made by MyPolymer, cells in more than 50% of filled wells are viable at 24 h after seeding even though the survival rate drops to about 20% at 48 h after seeding. However, for NOA, cells in more than 80% of filled wells are alive at 48 h after seeding no matter what coating configuration is used. The viability could sustain at more than 60% in microwells made by NOA polymer even at 96 h after seeding.

Example 4

Figure 4:
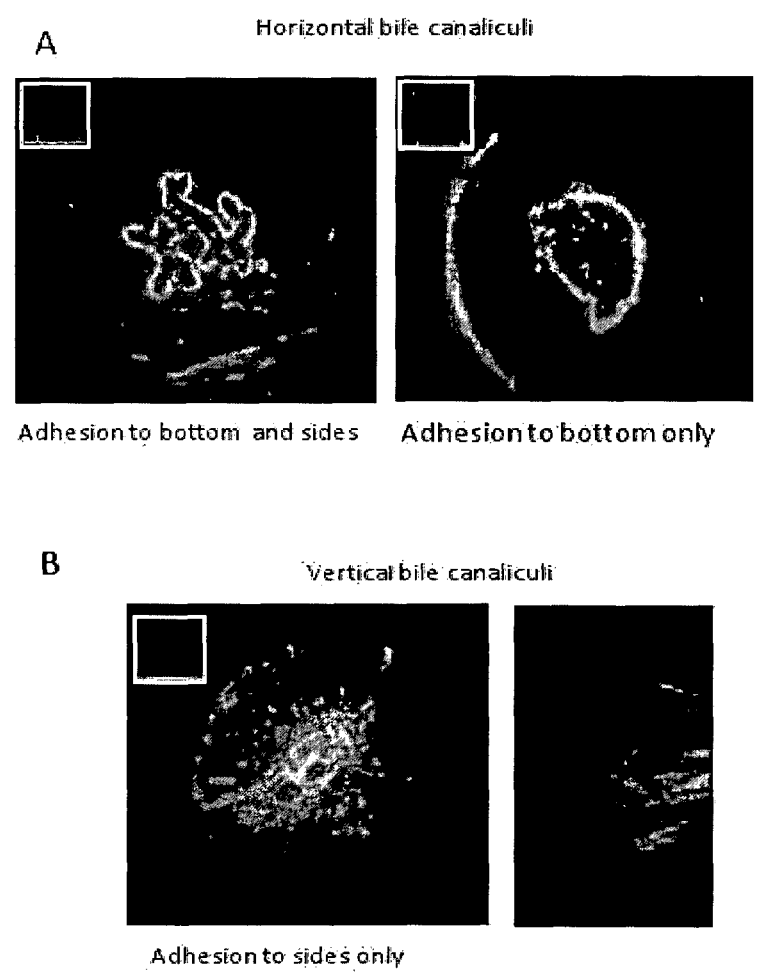

The hepatocytes can be fixed and stained with antibody within the wells. High resolution imaging within a single well without loss of optical resolution compared to normal culture conditions can then be performed. Live imaging with transfected protein is also possible. This offers the opportunity to monitor the evolution of a series of single doublets over time in a very easy way. As shown in FIG. 4 the morphology and orientation of the bile canaliculi can be tuned by changing the chemical coating of the wells. That property can be used to control the tension on the bile canaliculi and its correlation with drug testing. The formation of vertical canaliculi also allows high spatial and time resolution imaging of molecular transport from the cytoplasm to the bile duct. It is a first step towards the control of the formation of bile canaliculi spanning several cells. In addition the formation of vertical bile canaliculi makes it handier to collect bile secretion which is a key challenge for drug testing.

Example 5

Actomyosin contractility couples 3D cell-ECM adhesion to BC morphologies between hepatocyte couplets.

Figure 5:
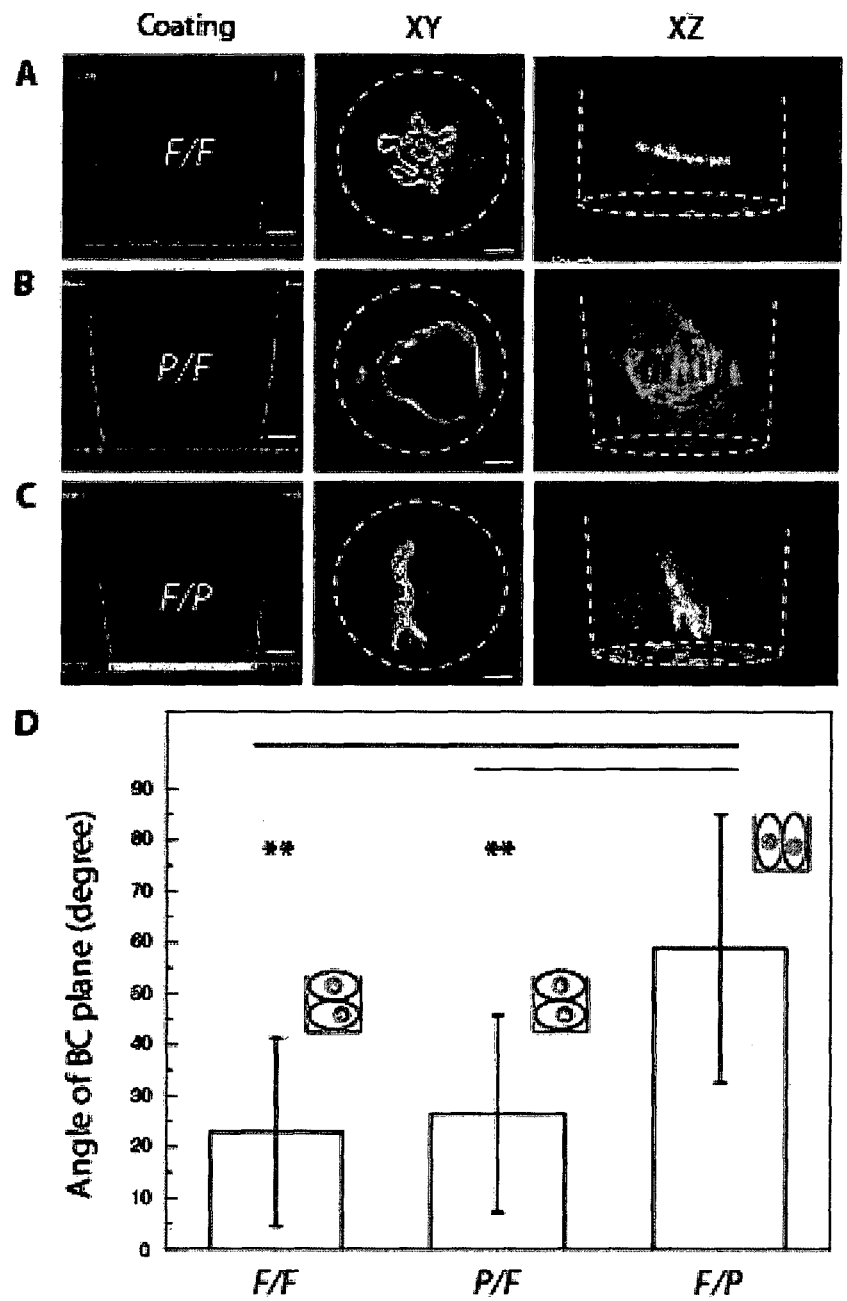

We investigated how the 3D adhesion of hepatocyte couplets to ECM influenced BC morphology. We chose 30 µm circular microwells to maximize the efficiency of couplet formation of hepatocytes, which have an average diameter of 25 µm. Cells were fixed on day 2, stained for F-actin and ZO-1, and imaged by confocal microscopy. Because F-actin signal provides a clearer definition of BC contour than ZO-1 (FIG. 11), we choose F-actin as a marker to demonstrate and quantify BC morphology in this work. The three ECM coating configurations induced three different BC morphologies (FIG. 5).

When the side and bottom of microwells were ECM-coated (F/F configuration), the couplet became stacked vertically (FIG. 5A, 5D). The bottom cell adhered both to the bottom and side of the microwell, whereas the top cell adhered to the side only. The BC exhibited a flat (2-3 µm) isotropic tubular morphology localizing at the centre of the cell-cell junction. This is reminiscent of the BC morphology observed in vivo [23].

Figure 12:
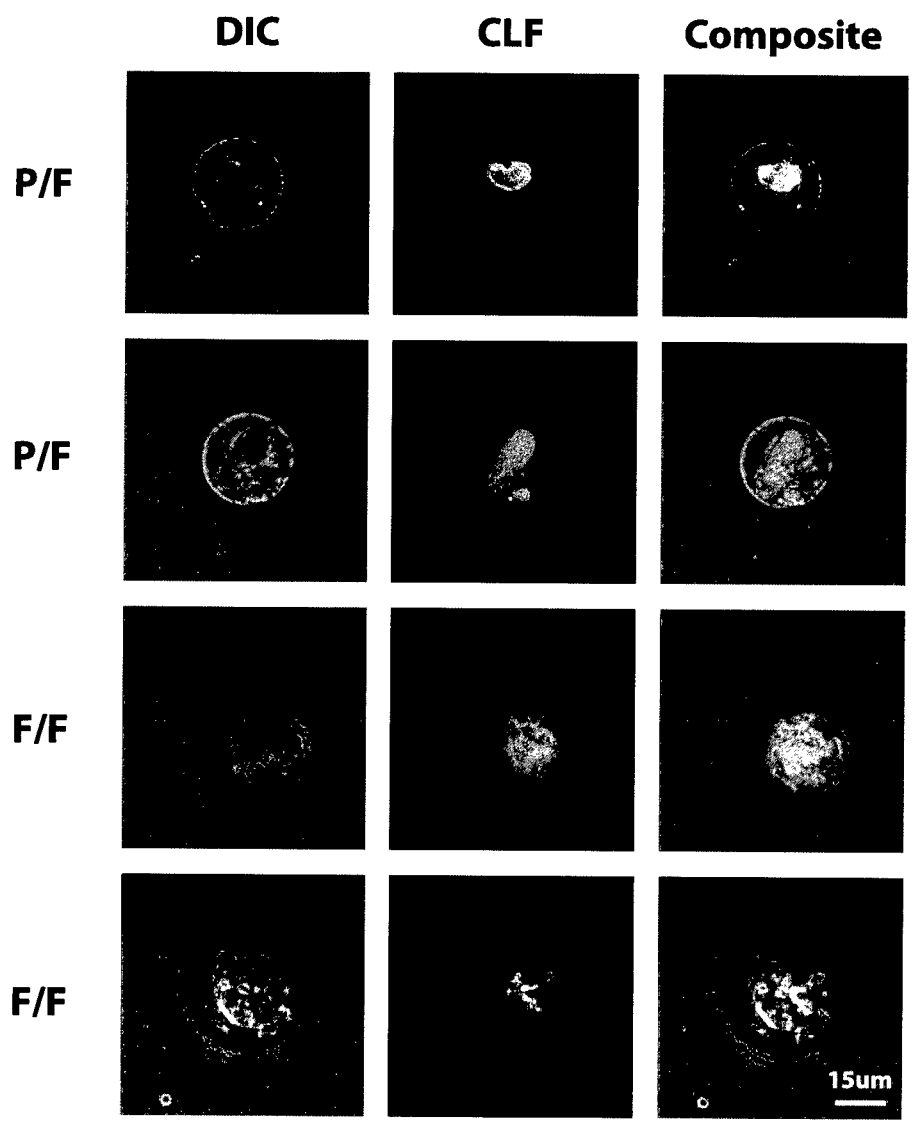
FIG. 12 illustrates the excretion of bile canaliculi in the microwell device.

When the microwell bottom was ECM-coated and the side was non-adhesive (P/F configuration), the couplet also remained stacked (FIG. 5B, 5D). Only the bottom cell of vertical couplet adhered to the bottom of microwell. The BC exhibited a large spherical morphology (5 to 15 µm) with few folds and villi, which is similar to the BC observed in freshly extracted couplets [26] or small organoids [27]. The BC with any morphology remained functional in microwells, which was confirmed by CLF test (FIG. 12).

Figure 6:
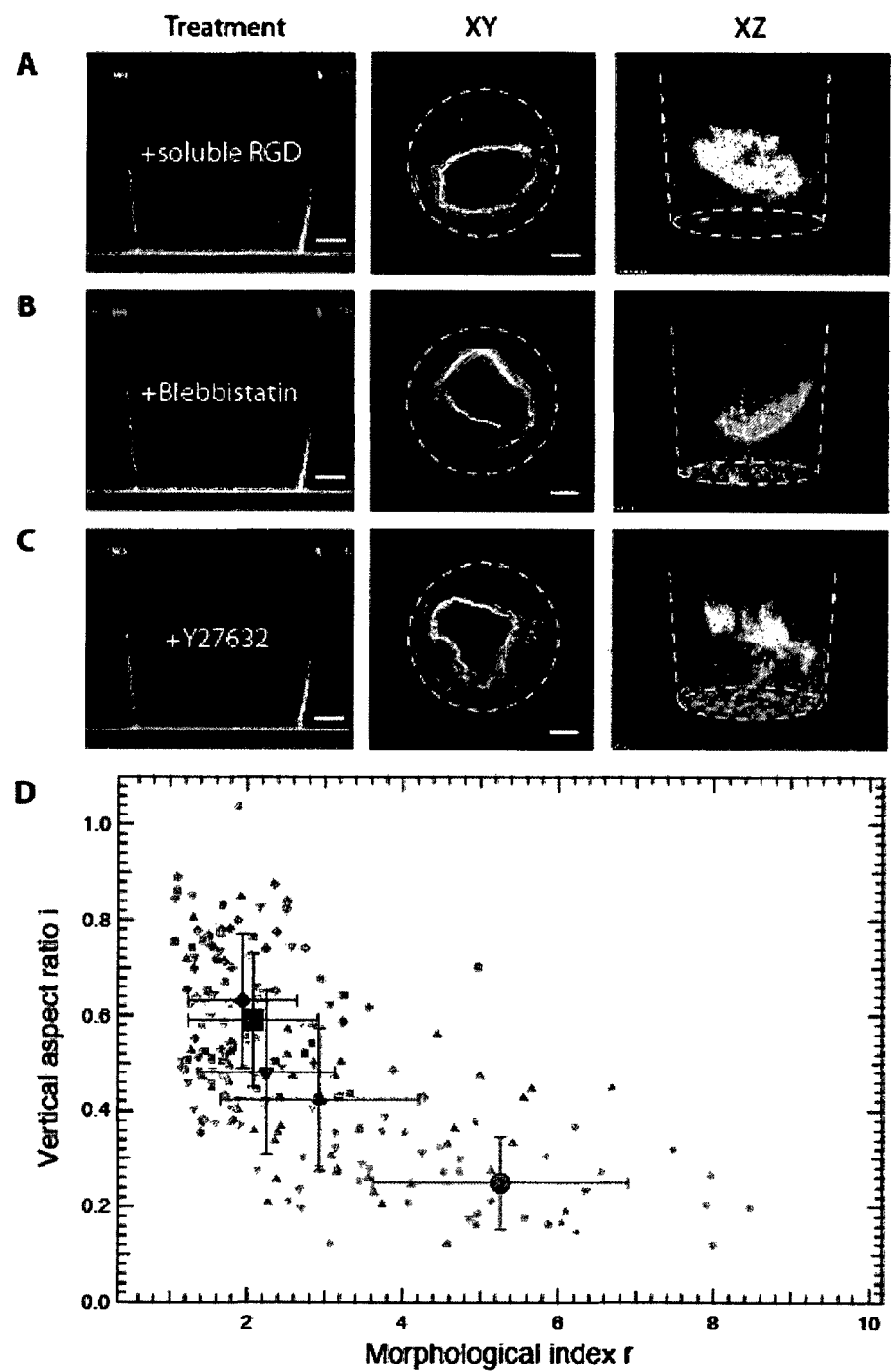

When cells adhered to the side of microwell only (F/P configuration), hepatocytes positioned side by side (FIG. 5C, 5D). The BC formed vertically, spanning most of the cell-cell contact area, exhibiting a flat morphology (2-3 µm thick). Our observations suggested that the spatial organization of cell ECM adhesion could control the mesoscale morphology of BC. To confirm the importance of cell-ECM adhesion in obtaining flat tubular BC, we treated the hepatocytes in F/F microwells on day 1 with soluble RGD peptides (250 µM, overnight) that antagonized the integrin-mediated cell-ECM adhesion while keeping the chemical signalling unperturbed. Indeed, as cells detached from the microwells, their BC rounded up to be morphologically equivalent to those observed in the P/F case (FIG. 6A).

Cell-ECM interaction complex is intimately associated with actin cytoskeleton[28] and actomyosin contractility was shown to regulate BC dynamics [29]. Therefore, we tested whether actomyosin contractility was required for the differential control of BC morphology by the spatial organization of cell-ECM adhesion. We found that folded BC formed in F/F microwells rounded up upon inhibition of the myosin II activity through various pathways using blebbistatin (100 µM, 4 h) or Y27632 (10 µM, 4 h). The resulting morphologies were similar to those obtained in the P/F configuration (FIG. 6B, 6C).

The BC morphologies in different conditions were quantitatively assessed by two dimensionless parameters: the degree of folding and vertical aspect ratio. The degree of folding $r=P^2/(4\pi A)$ was evaluated by measuring the ratio of the BC projected perimeter P to the projected area A. This morphological index r ranges from 1 (circle) upward (folded tubular structures). The vertical aspect ratio i was calculated as the ratio of the BC maximal height over maximal elongation in the XY plane. Higher vertical aspect ratio represents a thicker BC.

When the degree of folding r was plotted versus the vertical aspect ratio i (FIG. 6D), the flat and tubular shape of BC in F/F microwells is reflected by a low vertical aspect ratio but a high degree of folding. In contrast, BC in P/F microwells, in F/F microwells with soluble RGD, in F/F microwells with blebbistatin, or in F/F microwells with Y27632 assumed a higher vertical aspect ratio and a lower degree of folding, characteristics of their inflated shape. The BC morphologies in F/F microwells group into a cluster clearly distinctive from the cases of the P/F configuration or the F/F configurations under drug treatments.

Example 6

Figure 7:
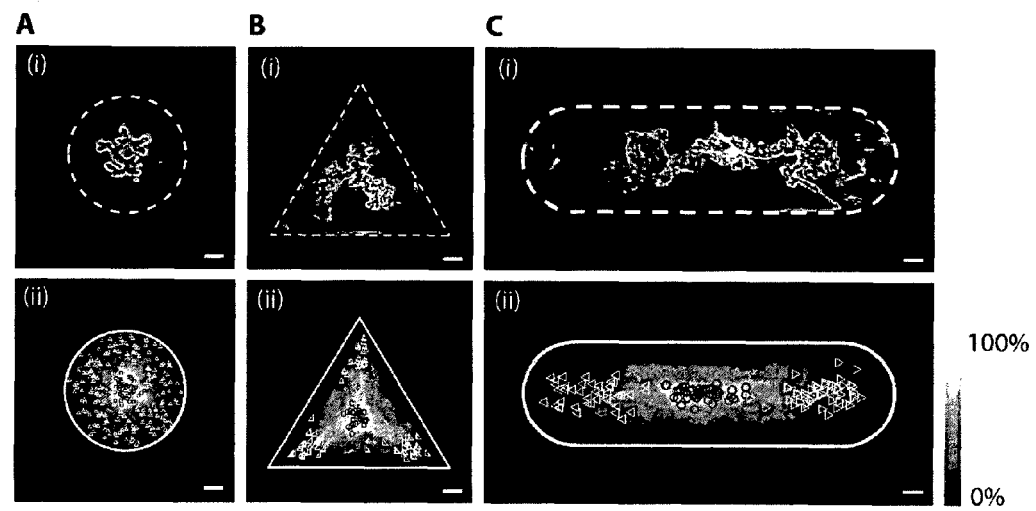

Physical Constraint Combined with Specific 3D ECM Organization Controls Bile Canaliculi Elongation Since actomyosin contractility participates to the distant regulation of BC morphology by cell-ECM adhesion, we hypothesized that the BC elongation would be affected by physical constraint, which is known to regulate actomyosin contractility [30]. Microwells with different shapes were utilized to impose physical constraint and modulate the actomyosin contractility. We seeded hepatocytes in F/F coated equilateral triangular microwells (45 µm side) since actomyosin contractility is developed in the vicinity of vertices by virtue of local actomyosin accumulation [31]. Two days after seeding, the hepatocytes remained stacked with their BC adopting a 3-lobed clover-leave shape pointing in the direction of the triangle vertices (FIG. 7B(i)). However, no BC formed in P/F triangle microwells since few couplets were observed (data not shown). Overlaying the binarized images of the BC after alignment of the microwell edges, we computed the probability of finding a BC at a given point of cell-cell contact inside triangle microwells (FIG. 7B(ii)). In addition, the distribution of the centres and the distribution of the most distant points of BC were also evaluated (FIG. 7B(ii)). It revealed that the average shape of BC was indeed a three-lobed structure with each branch extending towards a vertex of triangular microwell. As a control, we evaluated the probability map of BC in the round microwells in which the BC extension was isotropic (FIG. 7A(i)). The most possible BC shape in the circular microwells is a circle with its lobe ends distributed isotropically (FIG. 7A(ii)). Thus, these results supported that physical constraint could direct BC elongation via actomyosin contractility.

Figure 13:
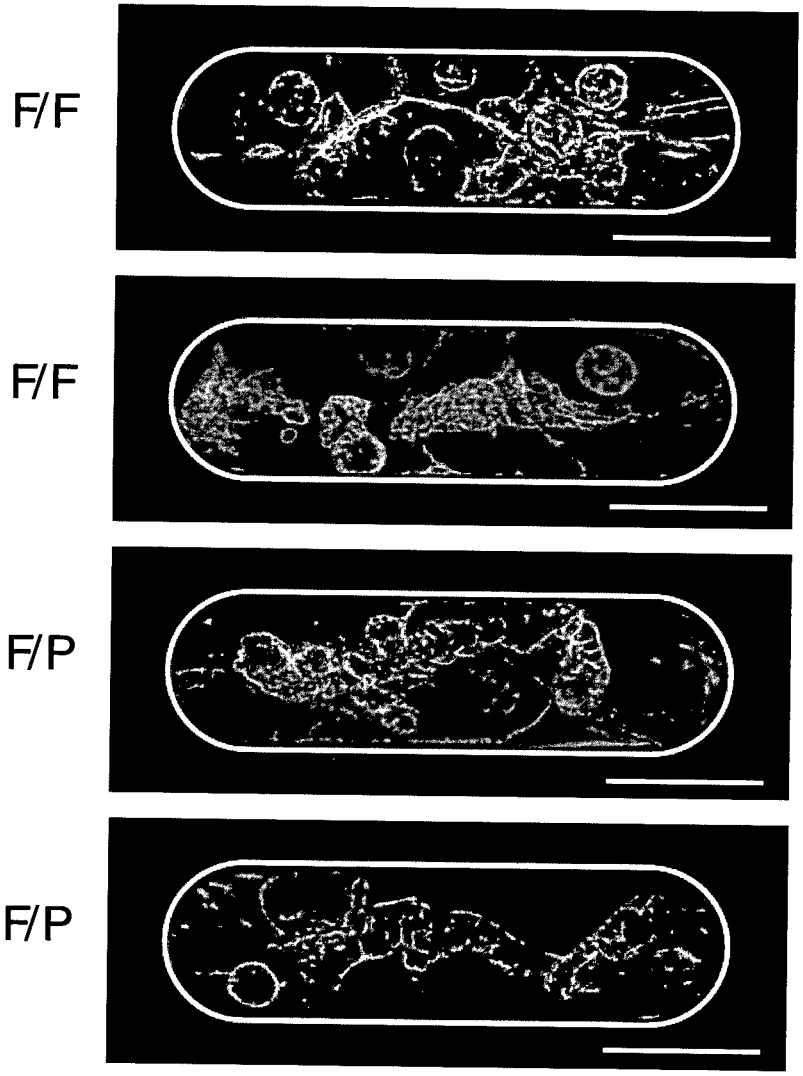
FIG. 13 illustrates the morphologies of bile canniculi in a microwell device comprising different surface coatings.

Cell-cell interaction is equivalently likely to affect actomyosin contractility as cell-ECM interaction [32]. Cell-cell interaction is thus expected to impact the BC morphologies. To test this hypothesis, we seeded multiple hepatocytes into elongated microwells (F/P) to alter the cell-cell contact status. Compared to other coating configurations, the F/P elongated microwells best ensured that cells spontaneously accommodate into two facing rows with vertical interfaces (FIG. 13). Flat vertical BC with transverse branches are expected based on our observations on couplets in similar coating configurations (FIG. 5C). However, BC adopted long tubular structures extending in the direction of the major axis of the elongated microwells (FIG. 7C (i)) with only small transverse branches. The probability map of BC in these elongated microwells clustered in the centre along the major axis of the microwells (FIG. 7C (ii)).

Figure 8:
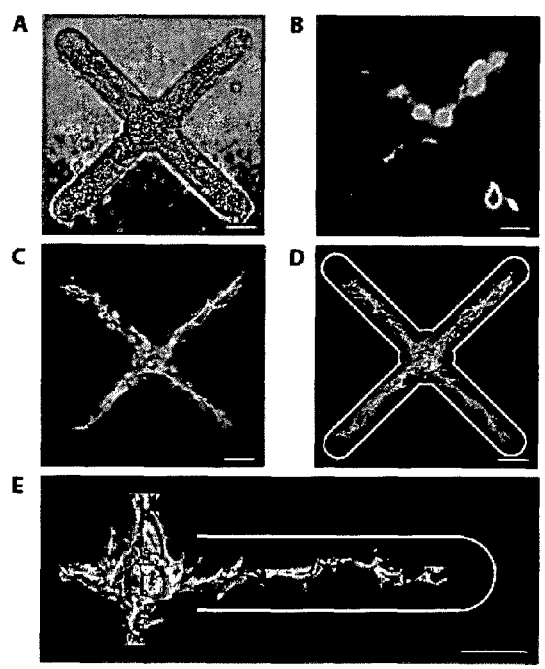

Taken together, our observations support the hypothesis that the actomyosin contractility, affected either by physical constraint, cell-ECM or cell-cell interactions, can determine the mesoscale BC morphology. We then developed a scaffolding biomechanical microenvironment with the combined effects of cell-cell/ECM interactions and physical constraint to control BC morphology. We mimicked hepatic cords using intersecting elongated microwells (30 µm wide and 300 µm long) with F/P coating configuration. We observed long functional bile canaliculi spanning the entire length of microwells (300 µm) (FIG. 8). This morphology was only observed in the F/P coating configuration with weak adhesion of hepatocytes on the bottom substrate, in which the actomyosin contractility likely distributed horizontally, thus connecting BC into elongated structures. The formed tubular network has similar dimension and morphology with a hepatic cord in vivo.

REFERENCES

1. Tokimitsu, Y., et al., *Single lymphocyte analysis with a microwell array chip*. Cytometry. Part A: the journal of the International Society for Analytical Cytology, 2007. 71(d7423775-bdc6-2ff3-6660-0ba53b91d33e): p. 1003-1013.
2. Frisk, T., et al., *A silicon-glass microwell platform for high-resolution imaging and high-content screening with single cell resolution*. Biomedical microdevices, 2011. 13(1 de755c2-6df9-44ea-c29e-0cd58a5e9531): p. 683-776.
3. Deutsch, M., et al., *A novel miniature cell retainer for correlative high-content analysis of individual untethered non-adherent cells*. Lab on a chip, 2006. 6(3276c364-c090-f983-f157-0ba20fe8322b): p. 995-1995.
4. Rettig, J. and A. Folch, *Large-scale single-cell trapping and imaging using microwell arrays*. Analytical chemistry, 2005. 77(7706a861-4581-32ea-9457-0ba411b501ca): p. 5628-5662.
5. Chin, V., et al., *Microfabricated platform for studying stem cell fates*. Biotechnology and bioengineering, 2004. 88(c19be9be-e822-408b-766b-0ba36cd9b0ac): p. 399-814.
6. Revzin, A., et al., *Development of a microfabricated cytometry platform for characterization and sorting of individual leukocytes*. Lab on a chip, 2005. 5(9975720d-12e8-4bf4-6a68-0ba3c645580b): p. 30-37.
7. Suh, K., et al., *A simple soft lithographic route to fabrication of poly(ethylene glycol) microstructures for protein and cell patterning*. Biomaterials, 2004. 25(ec2f0199-35bb-01a4-bcd5-0cd58c13d534): p. 557-620.
8. Matsui, H., et al., *Enhanced bile canaliculi formation enabling direct recovery of biliary metabolites of hepatocytes in 3D collagen gel microcavities*. Lab on a chip, 2012.

9. Jinno, S., et al., *Macrofabricated multilayer parylene-C stencils for the generation of patterned dynamic cocultures.* Journal of Biomedical Materials Research Part A, 2008. 86A(1): p. 278-288.
10. Taylor, L. and D. Walt, *Application of high-density optical microwell arrays in a live-cell biosensing system.* Analytical biochemistry, 2000. 278(90de4a92-d85b-ee87-eb38-0ba2fc6c99de): p. 132-174.
11. Ochsner, M., et al., *Micro-well arrays for 3D shape control and high resolution analysis of single cells.* Lab on a chip, 2007. 7(29a38e9e-c43c-0aa9-9324-0cd58c0442f9): p. 1074-1081.
12. Bartolo, D., et al., *Microfluidic stickers.* Lab on a chip, 2008. 8(f7cc4bb8-f855-9f90-366e-cc3ac0e05b6d): p. 274-283.
13. Morel, M., et al., *Microfluidic stickers for cell-and tissue-based assays in microchannels.* Lab on a chip, 2009. 9(a5211e5d-4f2c-45a7-d472-0baae240cf77): p. 1011-1014.
14. LeCluyse, E. L., K. L. Audus, and J. H. Hochman, *Formation of extensive canalicular networks by rat hepatocytes cultured in collagen-sandwich configuration.* The American journal of physiology, 1994. 266(6 Pt 1): p. C1764-74.
15. Moeller, H.-C., et al., *A microwell array system for stem cell culture.* Biomaterials, 2008. 29(ca0b5d0c-26cd-4c34-6581-d4e27d789b91): p. 752-815.
16. Håkanson, M., M. Textor, and M. Charnley, *Engineered 3D environments to elucidate the effect of environmental parameters on drug response in cancer.* Integrative biology: quantitative biosciences from nano to macro, 2011. 3(c1bf7ea3-a818-e378-becd-0cd58bf4f5eb): p. 31-39.
17. Evenou, F., T. Fujii, and Y. Sakai, *Spontaneous formation of stably-attached and 3D-organized hepatocyte aggregates on oxygen-permeable polydimethylsiloxane membranes having 3D microstructures.* Biomedical microdevices, 2010. 12(3): p. 465-75.
18. Nakazawa, K., et al., *Hepatocyte spheroid culture on a polydimethylsiloxane chip having microcavities.* Journal of biomaterials science. Polymer edition, 2006. 17(8): p. 859-73.
19. Khetani, S. R. and S. N. Bhatia, *Microscale culture of human liver cells for drug development.* Nature biotechnology, 2008. 26(1): p. 120-6.
20. Fukuda, J. and K. Nakazawa, *Hepatocyte spheroid arrays inside microwells connected with microchannels.* Biomicrofluidics, 2011. 5(7aa3c3f9-f0b0-8304-fbe5-0bb9e17f273c): p. 22205.
21. Okuyama, T., et al., *Preparation of arrays of cell spheroids and spheroid-monolayer cocultures within a microfluidic device.* Journal of bioscience and bioengineering, 2010. 110(aa6b4230-b89c-5577-a46a-0bb9e17f7760): p. 572-578.
22. Fry, J. R., et al., *The enzymic isolation of adult rat hepatocytes in a functional and viable state.* Analytical biochemistry, 1976. 71(2): p. 341-50.
23 S. Hoehme, M. Brulport, A. Bauer, E. Bedawy, W. Schormann, M. Hermes, V. Puppe, R. Gebhardt, S. Zellmer, M. Schwarz, E. Bockamp, T. Timmel, J. G. Hengstler, and D. Drasdo, *Proc. Natl. Acad. Sci. U.S.A.,* 2010, 107, 10371-10376.
24. T. Masters, W. Engl, Z. L. Weng, B. Arasi, N. Gauthier, and V. Viasnoff, *PLoS ONE,* 2012, 7, e44261.
25. D. Bartolo, G. Degré, P. Nghe, and V. Studer, *Lab Chip,* 2008, 8, 274-279.
26. T. Kitamura, U. Brauneis, Z. Gatmaitan, and I. M. Arias, *Hepatology,* 1991, 14, 640-647.
27. S. F. Abu-Absi, J. R. Friend, L. K. Hansen, and W.-S. Hu, *Experimental Cell* Research, 2002, 274, 56-67.
28. A. Ben-Ze'ev, G. S. Robinson, N. Bucher, and S. R. Farmer, *Proceedings of the National Academy of Sciences,* 1988, 85, 2161.
29. H. Kawahara and S. W. French, *Am. J. Pathol.,* 1990, 136, 521-532.
30. M. Théry, V. Racine, M. Piel, A. Pépin, A. Dimitrov, Y. Chen, J.-B. Sibarita, and M. Bornens, *Proceedings of the National Academy of Sciences,* 2006, 103, 19771-19776.
31. N. C. Rivron, E. J. Vrij, J. Rouwkema, S. Le Gac, A. van den Berg, R. K. Truckenmüller, and C. A. van Blitterswijk, *Proc. Natl. Acad. Sci. U.S.A.,* 2012, 109, 6886-6891.
32. G. A. Gomez, R. W. McLachlan, and A. S. Yap, *Trends Cell Biol.,* 2011, 21, 499-505.
33. P. O. Seglen, *Methods Cell Biol.,* 1976, 13, 29-83

The invention claimed is:
1. A cell culture vessel comprising a three dimensional cell culture substrate comprising:
    a perforated membrane with through holes,
    the perforated membrane having three membrane surfaces, namely an upper surface, a lower surface opposite to the upper surface, and a plurality of inner surfaces inside the through holes,
    the perforated membrane comprising a cured polymer adapted for cell culture having at least two modified cell culture surfaces among the three surfaces of the perforated membrane,
    wherein the first cell culture surface comprises at least one first cell culture agent for enhancing the proliferation and/or differentiation or function of the cells and the second cell culture surface does not comprise the first cell culture agent but a second different cell culture agent for enhancing the proliferation and/or differentiation or function of the cells,
    the first and the second cell culture surfaces being two surfaces out of the three membrane surfaces.
2. The cell culture vessel of claim 1, further comprising at least one cell, and cell culture medium.
3. The cell culture vessel according to claim 2, wherein said cell culture substrate is suspended and supported in said cell culture medium.
4. The cell culture vessel according to claim 3, wherein said cell culture substrate comprises one or more cell culture surfaces, wherein said cell culture surfaces do not contact a cell culture vessel surface.
5. The cell culture vessel according to claim 4, wherein said cell is genetically modified by transfection with an isolated nucleic acid or expression vector to recombinantly express a selected nucleic acid in said cell.
6. The cell culture vessel according to claim 1, wherein said cell is a mammalian cell or a prokaryotic cell.
7. The cell culture vessel according to claim 6, wherein said mammalian cell is an epidermal keratinocyte, a fibroblast cell, an epithelial cell, a neuronal glial cell, a neural cell, a hepatocyte, a hepatocyte stellate cell, a mesenchymal cell, a muscle cell, a kidney cell, a blood cell, a pancreatic β cell, cancer cell, or an endothelial cell.
8. The cell culture vessel according to claim 1, wherein said membrane comprises a plurality of perforations wherein said perforations are at least 5-1000 µm in diameter.
9. The cell culture vessel according to claim 8, wherein the perforations have an aspect ratio not greater than 2.
10. The cell culture vessel according to claim 1, wherein said curable polymer is UV curable.

11. The cell culture vessel according to claim 10, wherein said UV curable polymer is an acrylate based polymer.

12. The cell culture vessel according to claim 1, wherein said cell culture agent and/or said membrane is further modified by inclusion of a cross-linking agent that facilitates the cross-linking of the cell culture agent to said membrane to provide a modified cell culture surface.

13. The cell culture vessel according to claim 1, wherein said membrane has a refractive index of between about 1.30 to about 1.50.

14. The cell culture vessel according to claim 1, wherein said cell substrate comprises a network of interconnected cell culture microwells.

15. The cell culture vessel according to claim 14, wherein the network comprises a plurality of elongate cell culture microwells adapted to provide at least said first and second modified cell culture surfaces.

16. A method for the culture of cells, comprising:
  i) providing a cell culture vessel according to claim 1, comprising:
    a) cells; and
    b) cell culture medium sufficient to support the growth of said cells; and
  ii) providing cell culture conditions which promote the proliferation and/or differentiation and/or function of said cells.

17. The method according to claim 16, wherein said cell culture substrate is suspended and supported in said cell culture medium.

18. The method according to claim 17 wherein said cell culture substrate comprises one or more cell culture surfaces wherein said cell culture surface does not contact a cell culture vessel surface.

19. A method to screen for an agent that affects the proliferation, differentiation or function of a cell, comprising:
  i) providing a cell culture comprising at least one cell and a cell culture vessel according to claim 1;
  ii) adding at least one agent to be tested; and
  iii) monitoring the activity of the agent with respect to the proliferation, differentiation or function of said cells.

20. A method to test the liver toxicity of an agent, comprising:
  i) providing a cell culture comprising at least one hepatocyte cell and a cell culture vessel according to claim 1;
  ii) adding at least one agent to be tested; and
  iii) monitoring the activity of the agent with respect to the proliferation, differentiation or function of said hepatocyte cells as a measure of toxicity of the agent.

* * * * *